US011684642B2

(12) United States Patent
Jeon et al.

(10) Patent No.: US 11,684,642 B2
(45) Date of Patent: Jun. 27, 2023

(54) **COMPOSITION FOR THE TREATMENT OF ATOPIC DERMATITIS COMPRISING *BIFIDOBACTERIUM ANIMALIS* SUBSP. *LACTIS* LM1017**

(71) Applicants: LACTOMASON CO., LTD., Jinju-si (KR); GENOME AND COMPANY, Seongnam-si (KR)

(72) Inventors: Min Gyu Jeon, Jinju-si (KR); Shin Young Park, Yongin-si (KR); Yun Yeon Kim, Seoul (KR)

(73) Assignees: LACTOMASON CO., LTD., Jinju-si (KR); GENOME AND COMPANY, Seongnam-si (KR)

( * ) Notice: Subject to any disclaimer, the term of this patent is extended or adjusted under 35 U.S.C. 154(b) by 51 days.

(21) Appl. No.: 15/734,900

(22) PCT Filed: Nov. 11, 2020

(86) PCT No.: PCT/KR2020/015774
§ 371 (c)(1),
(2) Date: Dec. 3, 2020

(87) PCT Pub. No.: WO2021/132879
PCT Pub. Date: Jul. 1, 2021

(65) Prior Publication Data

US 2021/0361723 A1 Nov. 25, 2021

(30) Foreign Application Priority Data

Dec. 23, 2019 (KR) ........................ 10-2019-0173156

(51) Int. Cl.
*A61K 35/745* (2015.01)
*A23L 33/135* (2016.01)
*A61P 17/00* (2006.01)

(52) U.S. Cl.
CPC .......... *A61K 35/745* (2013.01); *A23L 33/135* (2016.08); *A61P 17/00* (2018.01); *A23V 2002/00* (2013.01); *A23Y 2300/21* (2013.01)

(58) Field of Classification Search
CPC combination set(s) only.
See application file for complete search history.

(56) References Cited

U.S. PATENT DOCUMENTS

2009/0060962 A1 3/2009 Castiel et al.
2019/0282636 A1* 9/2019 Lopez

FOREIGN PATENT DOCUMENTS

CN 110214014 A * 9/2019 .............. A61P 17/00
KR 10-2014-0066148 A 5/2014
KR 10-2017-0010270 A 1/2017
KR 1020190095173 A 8/2019
KR 10-2136346 B1 7/2020

OTHER PUBLICATIONS

Vibrio parahaemolyticus scrABC, a Novel Operon Affecting Swarming and Capsular Polysaccharide Regulation, Blaise R. Boles and Linda L. McCarter, Jul. 30, 2002 (Year: 2002).*
Makrgeorgou A, Leonardi-Bee J, Bath-Hextall FJ, Murrell DF, Tang ML, Roberts A, Boyle RJ. Probiotics for treating eczema. Cochrane Database Syst Rev. Nov. 21, 2018;11(11):CD006135. doi: 10.1002/14651858.CD006135.pub3. PMID: 30480774; PMCID: PMC6517242. (Year: 2018).*
Zhonggui Wang et al. (2011). Secreted factors from Bifidobacterium animalis subsp. lactis inhibit NF-κB-mediated interleukin-8 gene expression in Caco-2 cells. Applied and environmental microbiology, 77(22), 8171-8174. (Year: 2011).*
International Search Report, issued in the corresponding International Patent Application No. PCT/KR2020/015774, dated Feb. 17, 2021, 4 pages.
Ezendam et al., "Effects of Bifidobacterium animalis administered during lactation on allergic and autoimmune responses in rodents", Clinical and Experimental Immunology. 154. pp. 424-431 (2008).

* cited by examiner

*Primary Examiner* — Louise W Humphrey
*Assistant Examiner* — Kimberly C. Breen
(74) *Attorney, Agent, or Firm* — Hamre, Schumann, Mueller & Larson, P.C.

(57) ABSTRACT

A composition for the treatment of atopic dermatitis, the composition including, as an active ingredient, *Bifidobacterium animalis* subsp. *lactis* LM1017, and more specifically provided is a composition for the treatment of atopic dermatitis. The composition includes, as an active ingredient, a navel *Bifidobacterium animalis* subsp. *lactis* LM1017 which adjusts the NF-κB signal transduction pathway, and thus inhibits the expression of proinflammatory cytokines.

6 Claims, 11 Drawing Sheets

COMPOSITION FOR THE TREATMENT OF ATOPIC DERMATITIS COMPRISING *BIFIDOBACTERIUM ANIMALIS* SUBSP. *LACTIS* LM1017

This application claims the benefit under 35 USC 119(a) of Korean Patent Application No. 10-2019-0173156 filed on Dec. 23, 2019 in the Korean Intellectual Property Office, the entire disclosure of which is incorporated herein by reference for all purposes.

TECHNICAL FIELD

The present disclosure relates to a composition for the prevention and treatment of atopic dermatitis, containing *Bifidobacterium animalis* subsp. *lactis* LM1017 and more particularly, to a composition for the prevention and treatment of atopic dermatitis, containing *Bifidobacterium animalis* subsp. *lactis* LM1017 that inhibits the expression level and inflammatory response of inflammatory cytokines by regulating an NF-κB signaling pathway.

BACKGROUND

Dermatitis refers to histological phenomena such as spongiosis of the epidermis, infiltration of inflammatory cells, vascular proliferation and vasodilation in the hypodermis, and infiltration of perivascular inflammatory cells. Dermatitis is classified into atopic dermatitis, contact dermatitis and seborrheic dermatitis, and people with dermatitis may suffer from pain caused by itching, erythema, swelling, and oozing and also suffer from emotional distress caused by the gaze of others, which results in difficulty in social adaptation.

Among them, atopic dermatitis is a chronic and recurrent inflammatory skin disease. Atopic dermatitis is a complex clinical syndrome caused by a combination of hereditary and environmental factors and having various appearances, and, thus, the cause of atopic dermatitis is difficult to define precisely. However, environmental factors including environmental pollution such as smoke, intake of food additives and an increase in allergens such as dust mite caused by an increase in room temperature, and hereditary factors including family history and skin barrier disorder are considered as main causes.

There are methods for treating atopic dermatitis, including the use of moisturizer, taking medicine, photochemotherapy and the like. However, chemical drugs, when taken for a long time, may cause side effects such as atrophy and swelling of the skin, expansion of vessels and pores and skin discoloration, and atopic dermatitis can develop into chronic disease with alternate periods of activity and inactivity due to its chronic and recurrent characteristics.

Accordingly, atopic dermatitis drugs derived from natural substances safe for humans with less side effects are being researched.

PRIOR ART DOCUMENT

Patent Document (Patent Document 1) Korean Patent Laid-open Publication No. 10-2019-0095173

DISCLOSURE OF THE INVENTION

Problems to be Solved by the Invention

The present disclosure provides a composition for the prevention and treatment of atopic dermatitis, containing

*Bifidobacterium animalis* subsp. *lactis* LM1017 that inhibits the expression of inflammatory cytokines or pro-inflammatory cytokines by regulating an NF-κB signaling pathway and thus inhibits an inflammatory response.

However, problems to be solved by the present disclosure are not limited to the above-described problems. Although not described herein, other problems to be solved by the present disclosure can be clearly understood by a person with ordinary skill in the art from the following description.

Means for Solving the Problems

An aspect of the present disclosure provides a composition for the prevention and treatment of atopic dermatitis, containing *Bifidobacterium animalis* subsp. *lactis* LM1017 [Depository Institution: Korean Culture Center of Microorganisms (KCCM), Accession Number: KCCM12629P, and Date of Deposit: Nov. 14, 2019].

Effects of the Invention

*Bifidobacterium animalis* subsp. *lactis* LM1017 according to an embodiment of the present disclosure can inhibit the expression of inflammatory cytokines or pro-inflammatory cytokines and reduce the number of mast cells and thus can be applied to food compositions, pharmaceutical compositions, cosmetic compositions or health functional foods which can be used for the prevention and treatment of atopic dermatitis.

Figure 1:
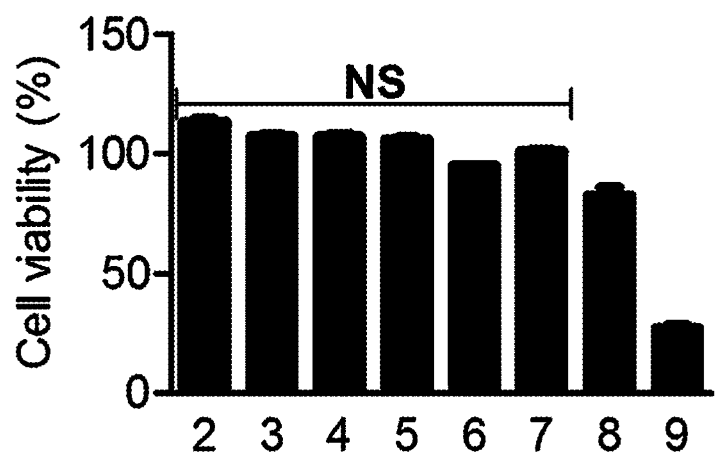
FIG. 1 is a graph showing the cell viability of RAW 264.7 cells with *Bifidobacterium animalis* subsp. *lactis* LM1017 [Depository Institution: Korean Culture Center of Microorganisms (KCCM), Accession Number: KCCM12629P, and Date of Deposit: Nov. 14, 2019] according to an example of the present disclosure.

*terium animalis* subsp. *lactis* LM1017 according to an example of the present disclosure.

BEST MODE FOR CARRYING OUT THE INVENTION

Hereafter, examples of the present disclosure will be described in detail with reference to the accompanying drawings so that the present disclosure may be readily implemented by a person with ordinary skill in the art. However, it is to be noted that the present disclosure is not limited to the examples but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected to" another element and an element being "electronically connected to" another element via another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereinafter, embodiments and examples of the present disclosure will be described in detail. However, the present disclosure may not be limited to the following embodiments and examples.

An aspect of the present disclosure provides a composition for the prevention and treatment of atopic dermatitis, containing *Bifidobacterium animalis* subsp. *lactis* LM1017 [Depository Institution: Korean Culture Center of Microorganisms (KCCM), Accession Number: KCCM12629P, and Date of Deposit: Nov. 14, 2019].

In an embodiment of the present disclosure, the composition for the prevention and treatment of atopic dermatitis may contain *Bifidobacterium animalis* subsp. *lactis* LM1017, heat-killed bodies, fragmented products, cultured products, concentrates or extracts thereof, and may contain, for example, heat-killed lactic acid bacteria obtained by heat treating *Bifidobacterium animalis* subsp. *lactis* LM1017, specifically heat-killed *Bifidobacterium animalis* subsp. *lactis* LM1017 obtained by culturing of *Bifidobacterium animalis* subsp. *lactis* LM1017 in a ceramic membrane bioreactor (MBR), which is a patent technology of LactoMason, and then tyndallization of *Bifidobacterium animalis* subsp. *lactis* LM1017 in a culture tank through batch heat treatment, but may not be limited thereto.

In an embodiment of the present disclosure, the composition for the prevention and treatment of atopic dermatitis may be a cosmetic composition, a pharmaceutical composition, or a health functional food. For example, the composition for the prevention and treatment of atopic dermatitis may be a cosmetic composition, a pharmaceutical composition, or a health functional food containing heat-treated *Bifidobacterium animalis* subsp. *lactis* LM1017, but may not be limited thereto.

In an embodiment of the present disclosure, the composition for the prevention and treatment of atopic dermatitis is not particularly limited to the amount of *Bifidobacterium animalis* subsp. *lactis* LM1017 long as it contains *Bifidobacterium animalis* subsp. *lactis* LM1017. For example, the composition may contain *Bifidobacterium animalis* subsp. *lactis* LM1017 at a concentration of from $1\times10^8$ cells/g to $1\times10^{10}$ cells/g, but may not be limited thereto. For example, the concentration of *Bifidobacterium animalis* subsp. *lactis* LM1017 may be in the range of from $1\times10^8$ cells/g to $1\times10^{10}$ cells/g, from $2\times10^8$ cells/g to $1\times10^{10}$ cells/g, from $3\times10^8$ cells/g to $1\times10^{10}$ cells/g, from $5\times10^8$ cells/g to $1\times10^{10}$ cells/g, from $1\times10^8$ cells/g to $5\times10^9$ cells/g, from $2\times10^8$ cells/g to $5\times10^9$ cells/g, from $3\times10^8$ cells/g to $5\times10^9$ cells/g, or from $5\times10^8$ cells/g to $5\times10^9$ cells/g, specifically $1\times10^9$ cells/g, but may not be limited thereto.

In an embodiment of the present disclosure, the composition for the prevention and treatment of atopic dermatitis is not particularly limited to the amount of *Bifidobacterium animalis* subsp. *lactis* LM1017 as long as it contains *Bifidobacterium animalis* subsp. *lactis* LM1017. For example, the composition may contain *Bifidobacterium animalis* subsp. *lactis* LM1017 at a concentration of from $1\times10^8$ cells/ml to $1\times10^{10}$ cells/ml, but may not be limited thereto. For example, the concentration of *Bifidobacterium animalis* subsp. *lactis* LM1017 may be in the range of from $1\times10^8$ cells/ml to $1\times10^{10}$ cells/ml, from $2\times10^8$ cells/ml to $1\times10^{10}$ cells/ml, from $3\times10^8$ cells/ml to $1\times10^{10}$ cells/ml, from $5\times10^8$ cells/ml to $1\times10^{10}$ cells/ml, from $1\times10^8$ cells/ml to $5\times10^9$ cells/ml, from $2\times10^8$ cells/ml to $5\times10^9$ cells/ml, from $3\times10^8$ cells/ml to $5\times10^9$ cells/ml, or from $5\times10^8$ cells/ml to $5\times10^9$ cells/ml, specifically $1\times10^9$ cells/ml, but may not be limited thereto.

In an embodiment of the present disclosure, *Bifidobacterium animalis* subsp. *lactis* LM1017 may inhibit the expression, generation and activity of inflammatory cytokines. For example, the inflammatory cytokines may include IL-6, IL-1β, TNF-α and IFN-γ, specifically IL-6 or IL-1@, but may not be limited thereto.

In an embodiment of the present disclosure, when the composition contains *Bifidobacterium animalis* subsp. *lactis* LM1017 at a concentration of from $1\times10^8$ cells/g to $1\times10^{10}$ cells/g, specifically $1\times10^9$ cells/g, the expression levels of IL-6 and/or IL-1@ as inflammatory cytokines may be decreased compared with a case where the composition does not contain *Bifidobacterium animalis* subsp. *lactis* LM1017, and, thus, the composition may have effects in treating or preventing atopic dermatitis, but may not be limited thereto.

In an embodiment of the present disclosure, when the composition contains *Bifidobacterium animalis* subsp. *lactis* LM1017 at a concentration of from $1\times10^8$ cells/ml to $1\times10^{10}$ cells/ml, specifically $1\times10^9$ cells/ml, the expression levels of IL-6 and/or IL-1@ as inflammatory cytokines may be decreased compared with a case where the composition does not contain *Bifidobacterium animalis* subsp. *lactis* LM1017, and, thus, the composition may have effects in treating or preventing atopic dermatitis, but may not be limited thereto.

In an embodiment of the present disclosure, *Bifidobacterium animalis* subsp. *lactis* LM1017 may inhibit the expression, generation and activity of pro-inflammatory cytokines. For example, *Bifidobacterium animalis* subsp. *lactis* LM1017 may inhibit an inflammatory response such as reducing the expression levels of inflammatory cytokines and/or pro-inflammatory cytokines by regulating an NF-κB signaling pathway, but may not be limited thereto.

In an embodiment of the present disclosure when the composition contains *Bifidobacterium animalis* subsp. *lactis* LM1017 at a concentration of from $1\times10^8$ cells/g to $1\times10^{10}$ cells/g, specifically $1\times10^9$ cells/g, an inflammatory response may be decreased by regulating the NF-κB signaling pathway compared with a case where the composition does not contain *Bifidobacterium animalis* subsp. *lactis* LM1017, and, thus, the composition may have effects in treating or preventing atopic dermatitis, but may not be limited thereto.

In an embodiment of the present disclosure, a pharmaceutical composition containing *Bifidobacterium animalis* subsp. *lactis* LM1017 may be formulated and used as formulations for oral administration such as powders, granules, tablets, capsules, suspensions, emulsions, syrups or aerosol, external preparations, suppositories or sterile injection solutions by conventional methods, respectively, but may not be limited thereto.

In an embodiment of the present disclosure, the pharmaceutical composition containing *Bifidobacterium animalis* subsp. *lactis* LM1017 may be formulated with generally used diluents or excipients such as fillers, extenders, binders, wetting agents, disintegrating agents or surfactants, but may not be limited thereto.

In an embodiment of the present disclosure, solid formulations for oral administration may include tablets, pills, powders, granules or capsules, and these solid formulations may be prepared by mixing *Bifidobacterium animalis* subsp. *lactis* LM1017 with at least one of excipients such as starch, calcium carbonate, sucrose, lactose or gelatin. Except for the simple excipients, lubricants such as magnesium stearate or talc may be used, but the present disclosure may not be limited thereto.

In an embodiment of the present disclosure, liquid formulations for oral administration may include suspensions, solutions for internal use, emulsions and syrups, and may contain various excipients such as wetting agents, sweeteners, aromatics and preservatives in addition to generally used simple diluents such as water and liquid paraffin, but may not be limited thereto.

In an embodiment of the present disclosure, formulations for parenteral administration may include sterilized aqueous solutions, water-insoluble excipients, suspensions, emulsions, lyophilized preparations and suppositories, but may not be limited thereto. For example, the water insoluble excipients or suspensions may contain propylene glycol, polyethylene glycol, vegetable oil such as olive oil, injectable ester such as ethylolate, and the like, but may not be limited thereto. For example, the suppositories may contain witepsol, macrogol, tween 61, cacao butter, laurin butter, glycerol, gelatin, and the like, but may not be limited thereto.

According to an embodiment of the present disclosure, the health functional food containing *Bifidobacterium animalis* subsp. *lactis* LM1017 may prevent or improve atopic dermatitis, but may not be limited thereto.

In an embodiment of the present disclosure, the health functional food containing *Bifidobacterium animalis* subsp. *lactis* LM1017 is not particularly limited in kind. *Bifidobacterium animalis* subsp. *lactis* LM1017 can be added to foods, for example, meats, sausages, breads, chocolates, candies, snacks, cookies, pizza, ramens, other noodles, gums, dairy products including ice cream, various kinds of soups, beverages, tea, drinks, alcohol drinks and vitamin complexes, but the present disclosure may not be limited thereto.

In an embodiment of the present disclosure, the health functional food containing *Bifidobacterium animalis* subsp. *lactis* LM1017 may be used in the form of pills, powders, granules, infusions, tablets, capsules, or drinks, and may include all health functional foods in the accepted meaning.

In an embodiment of the present disclosure, the health functional food containing *Bifidobacterium animalis* subsp. *lactis* LM1017 may contain various nutrients, vitamins, minerals (electrolytes), flavorants such as synthetic flavorants and natural flavorants, coloring agents, improving agents (cheese, chocolate, etc.), pectic acid and salts thereof, alginic acid and salts thereof, organic acids, protective colloidal thickeners, pH regulators, stabilizers, preservatives, glycerin, alcohols, carbonators used to be added to soda, etc., but may not be limited thereto.

In an embodiment of the present disclosure, the health functional food containing *Bifidobacterium animalis* subsp. *lactis* LM1017 may also include fruit flesh addable to natural fruit juices, fruit juice beverages and vegetable beverages, but may not be limited thereto. For example, all the above-described ingredients may be added individually or in combination.

In an embodiment of the present disclosure, the cosmetic composition containing *Bifidobacterium animalis* subsp. *lactis* LM1017 is not particularly limited in formulation and may have any one formulation selected from, for example, toner, lotion, essence, cream, pack, foundation and makeup base, but may not be limited thereto.

In an embodiment of the present disclosure, the cosmetic composition containing *Bifidobacterium animalis* subsp. *lactis* LM1017 may further contain any ingredient selected according to the formulation or purpose of use of cosmetics, but may not be limited thereto. For example, the cosmetic composition containing *Bifidobacterium animalis* subsp. *lactis* LM1017 may further contain purified water, oils, surfactants, moisturizing agents, higher alcohols, thickeners, chelating agents, pigments, fatty acids, preservatives, waxes, pH regulators, fragrances and the like, but may not be limited thereto.

In an embodiment of the present disclosure, if the formulation of the cosmetic composition containing *Bifidobacterium animalis* subsp. *lactis* LM1017 is paste, cream or gel, animal and vegetable fats, oils, waxes, paraffins, starch, tragacanth, cellulose derivatives, polyethylene glycols, silicones, bentonites, silica, talc or zinc oxide may be used as the carrier ingredient, but the present disclosure may not be limited thereto.

In an embodiment of the present disclosure, if the formulation of the cosmetic composition containing *Bifidobacterium animalis* subsp. *lactis* LM1017 is powder or spray, lactose, talc, silica, aluminum hydroxide, calcium silicates or polyamide powder may be contained as the carrier ingredient, and particularly, in the case of spray, it may further contain a propellant such as chlorofluorohydrocarbon, propane/butane or dimethyl ester, but may not be limited thereto.

In an embodiment of the present disclosure, if the formulation of the cosmetic composition containing *Bifidobacterium animalis* subsp. *lactis* LM1017 is a solution or an emulsion, solvents, solvating agents or emulsifying agents may used as the carrier ingredient, and examples thereof may include water, ethanol, isopropanol, ethyl carbonate, ethyl acetate, benzyl alcohol, benzyl benzoate, propylene glycol, 1,3-butylglycol oil, glycerol aliphatic ester, polyethylene glycol or sorbitan fatty acid ester, but may not be limited thereto.

In an embodiment of the present disclosure, if the formulation of the cosmetic composition containing *Bifidobacterium animalis* subsp. *lactis* LM1017 is a suspension, liquid diluting agents, such as water, ethanol or propylene glycol, suspending agents, such as ethoxylated isostearyl alcohol, polyoxyethylene sorbitol ester and polyoxyethylene sorbitan ester, microcrystalline cellulose, aluminum meta-hydroxide, bentonite, agar or tragacanth, etc. may be used as the carrier ingredient, but the present disclosure may not be limited thereto.

In an embodiment of the present disclosure, if the formulation of the cosmetic composition containing *Bifidobacterium animalis* subsp. *lactis* LM1017 is a surfactant-containing cleansing composition, aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oils, lanoline derivatives or ethoxylated glycerol fatty acid ester may be used as the carrier ingredient, but the present disclosure may not be limited thereto.

Hereinafter, the present disclosure will be explained in more detail with reference to Examples. However, the following Examples are illustrative only for better understanding of the present disclosure but do not limit the present disclosure.

EXAMPLES

Example 1: Preparation of Composition for Prevention and Treatment of Atopic Dermatitis Containing *Bifidobacterium animalis* Subsp. *lactis* LM1017

*Bifidobacterium animalis* subsp. *lactis* LM1017 according to the present example was prepared by batch culture.

The lactic acid bacteria were incubated in a 100 L fermenter (KoBioTech) with 60 L of culture medium, and the stirring rate was maintained at 30 rpm, the temperature was maintained at 35° C. to 37° C. and the pH was maintained at 5 to 6.5. After incubation, the culture medium was centrifuged at 13,000 rpm for 30 minutes to obtain the strain. The obtained strain was mixed with a cryoprotectant and then frozen in a cryogenic freezer for 24 hours and finally subjected to freeze-drying treatment to obtain *Bifidobacterium animalis* subsp. *lactis* LM1017.

Example 2: Cytotoxicity Assay of *Bifidobacterium animalis* Subsp. *lactis* LM1017

Cytotoxicity of *Bifidobacterium animalis* subsp. *lactis* LM1017 as obtained in Example 1 on cells was evaluated. The cells used herein were RAW 264.7 cells derived from mouse macrophage cells, and the RAW 264.7 cells were inoculated at a concentration of $1\times10^5$ cells/well into a 96-well cell culture plate. After incubation for 24 hours, the cells were treated with heat-treated *Bifidobacterium animalis* subsp. *lactis* LM1017 at different densities of $1\times10^2$, $1\times10^3$, $1\times10^4$, $1\times10^5$, $1\times10^6$, $1\times10^7$, $1\times10^8$, $1\times10^9$ cells/well and then incubated for 24 hours. The cell viability (%) depending on the concentration of the strain after incubation is shown in FIG. 1.

As shown in FIG. 1, it can be seen that the heat-treated *Bifidobacterium animalis* subsp. *lactis* LM1017 as obtained in the above-described Example did not affect the cell viability of the RAW 264.7 cells up to the concentration of $1\times10^7$ cells/well.

Example 3: Evaluation of Ability of *Bifidobacterium animalis* Subsp. *lactis* LM1017 to Regulate Expression of Inflammatory Cytokines The ability of *Bifidobacterium animalis* subsp. *lactis* LM1017 as obtained in Example 1 to regulate the expression of inflammatory cytokines was evaluated. The cells used herein were RAW 264.7 cells, and the RAW 264.7 cells were inoculated at a concentration of $1\times10^6$ cells/well into a 6-well cell culture plate. After incubation for 24 hours, the cells were treated for 1 hour with *Bifidobacterium animalis* subsp. *lactis* LM1017 at a non-toxic dosage of $1\times10^7$ cell/well as verified from the test result of Example 1 and preincubated. Then, the RAW 264.7 cells were treated for 24 hours with lipopolysaccharide (LPS) at a concentration of 1 μg/mL per well to induce an inflammatory response. Thereafter, the mRNA expression level of inflammatory cytokines treated with *Bifidobacterium animalis* subsp. *lactis* LM1017 according to Example 3 was compared with Comparative Examples not treated with *Bifidobacterium animalis* subsp. *lactis* LM1017, LPS or both of them, respectively, by using Real-Time PCR and the result thereof is shown in FIG. 2.

Figure 2A:
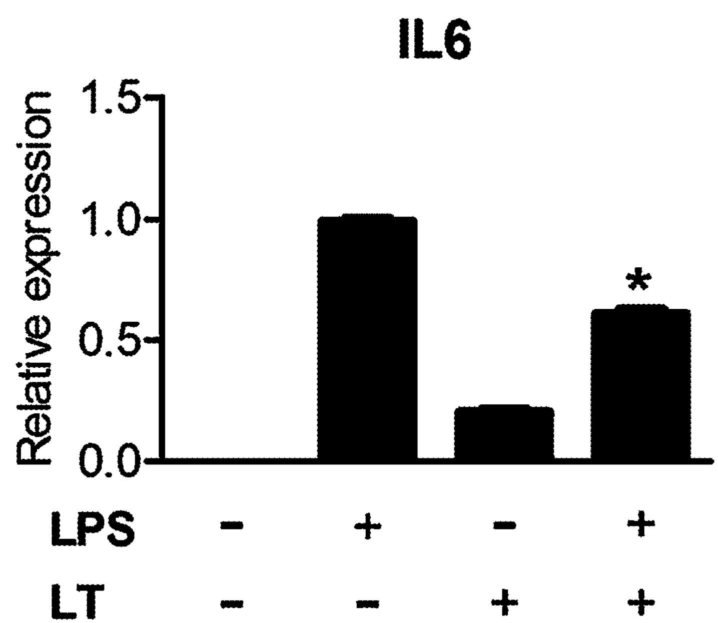
FIG. 2A and FIG. 2B are graphs showing the effect of regulating the expression levels of IL-6 and IL-1β mRNA by *Bifidobacterium animalis* subsp. *lactis* LM1017 according to an example of the present disclosure in RAW 264.7 cells and inflammation induced RAW 264.7 cells with LPS.
Figure 2B:
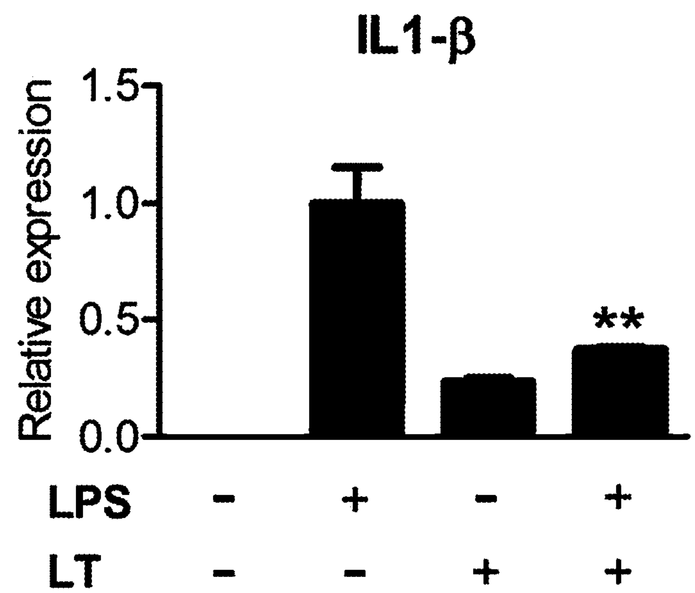

As shown in FIG. 2, it can be seen that Example 3 containing *Bifidobacterium animalis* subsp. *lactis* LM1017 significantly decreases the IL-6 mRNA and IL-1β mRNA expression levels in the LPS-induced RAW 264.7 cells. According to the result, it can be seen that *Bifidobacterium animalis* subsp. *lactis* LM1017 of the present disclosure can inhibit the expression of inflammatory cytokines, and, thus, the strain can inhibit an inflammatory response.

Example 4: Evaluation of Ability of *Bifidobacterium animalis* Subsp. *lactis* LM1017 to Regulate NF-κB Signaling Pathway The ability of *Bifidobacterium animalis* subsp. *lactis* LM1017 as obtained in Example 1 to regulate an NF-κB signaling pathway and the resultant expression of pro-inflammatory cytokines was evaluated. First, RAW 264.7 cells were inoculated at a concentration of $2\times10^6$ cells/well into a 100-mm culture plate. After incubation for 24 hours, the cells were treated for 1 hour with *Bifidobacterium animalis* subsp. *lactis* LM1017 at a non-toxic dosage of $1\times10^7$ cell/well as verified from the test result of Example 2 and preincubated. After preincubation, the RAW 264.7 cells were treated for 24 hours with LPS at a concentration of 1 μg/mL to induce an inflammatory response. After preincubation, the mRNA expression level of agents related to the NF-κB signaling pathway according to Example 4 was compared with Comparative Examples not treated with *Bifidobacterium animalis* subsp. *lactis* LM1017, LPS or both of them, respectively, and the result thereof is shown in FIG. 3.

As shown in FIG. 3, it can be seen that *Bifidobacterium animalis* subsp. *lactis* LM1017 does not affect the expression level of p65 ($p<0.05$, FIG. 3A) and inhibits the phosphorylation of IκB-α ($p<0.01$, FIG. 3C) but increases the expression level of IκB-α ($p<0.01$, FIG. 3B), compared with Comparative Example treated with LPS only.

Figure 3A:
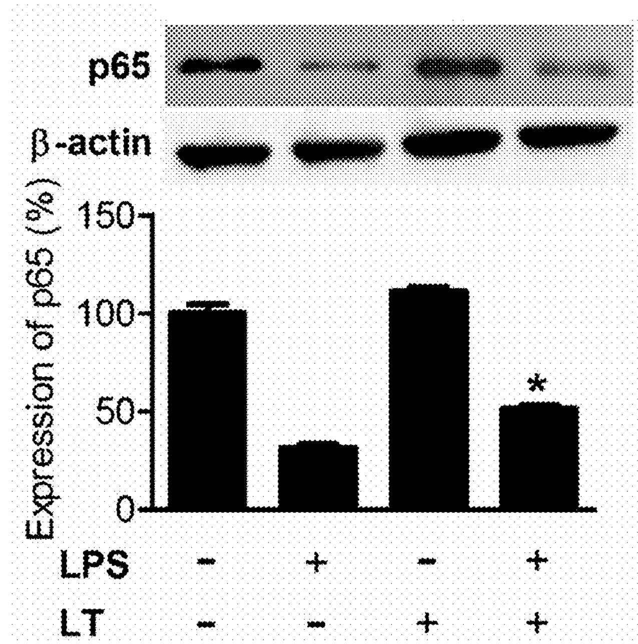
FIG. 3A to FIG. 3C are graphs showing the effect of regulating the expression levels of p65, IκB-α, and p-IκB-α by *Bifidobacterium animalis* subsp. *lactis* LM1017 according to an example of the present disclosure in RAW 264.7 cells and inflammation induced RAW 264.7 cells with LPS.
Figure 3B:
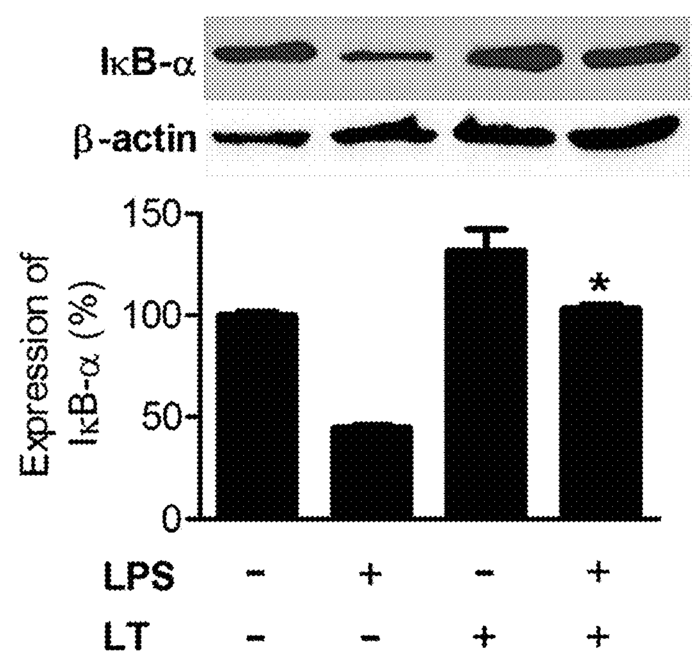
Figure 3C:
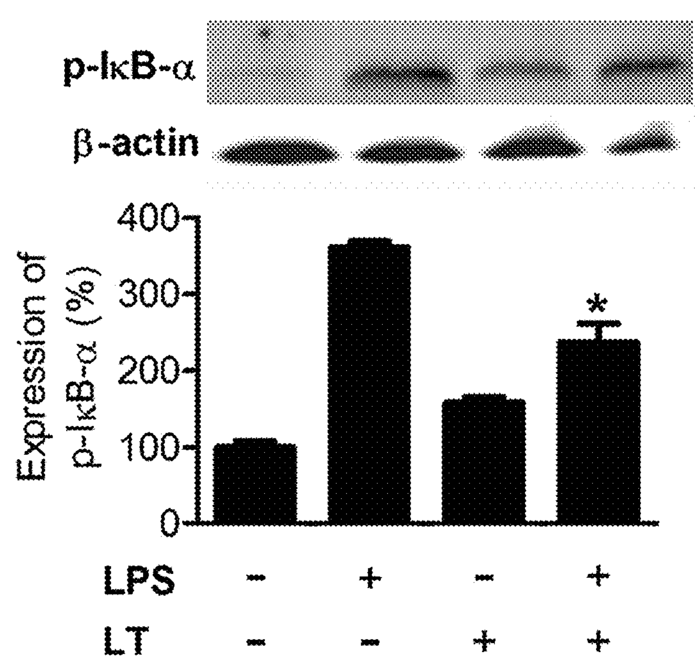
Figure 3D:
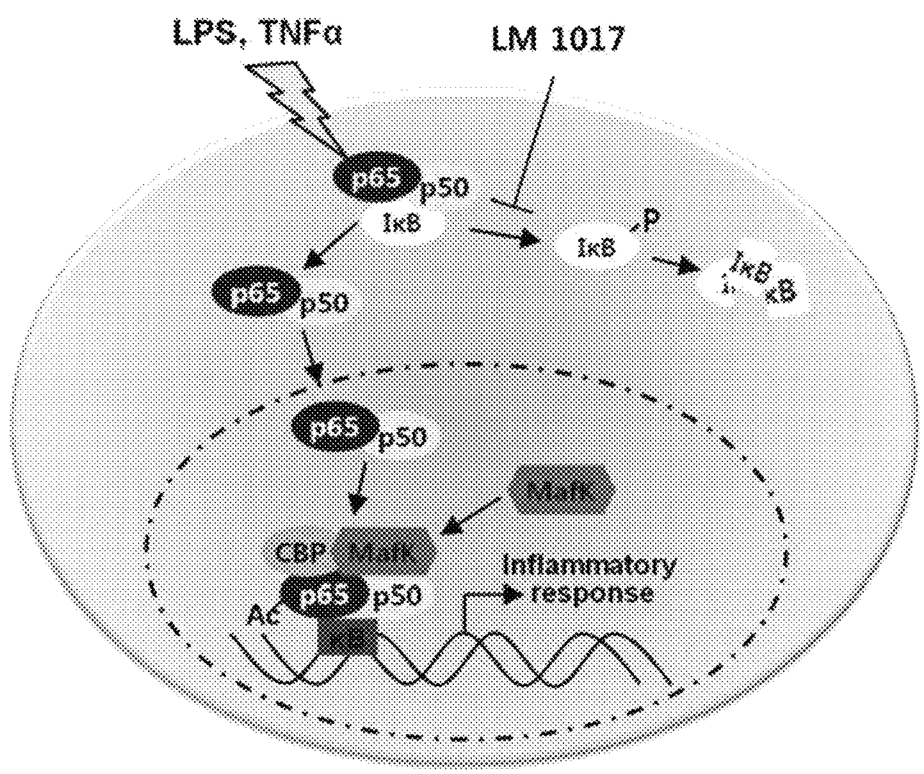
FIG. 3D illustrates a correlation between *Bifidobacterium animalis* subsp. *lactis* LM1017 and an NF-κB signaling pathway.
Figure 4A:
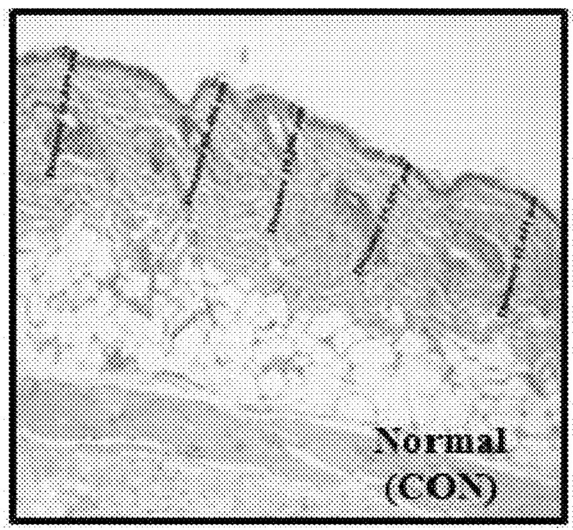
FIG. 4 provides optical microscopy images showing the result of H&E staining of the mouse skin treated with *Bifidobacterium animalis* subsp. *lactis* LM1017 according to an example of the present disclosure.
Figure 4B:
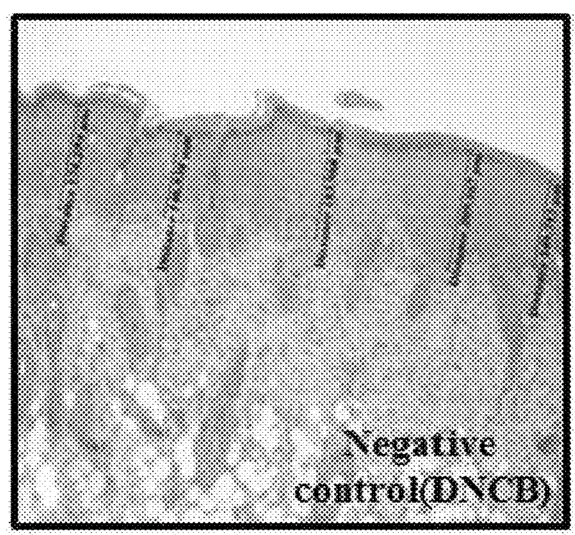
Figure 4C:
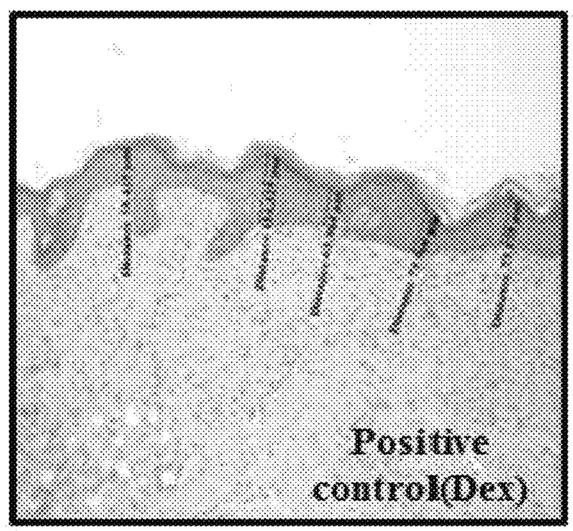
Figure 4D:
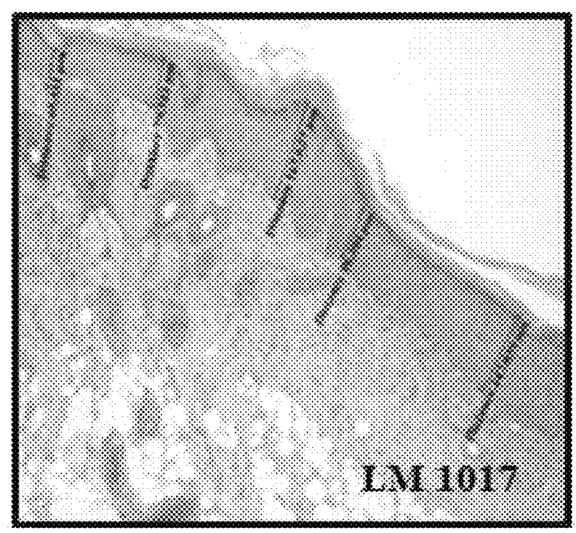

The result shows that LM1017 of the present disclosure inhibits the phosphorylation of IκB-α to suppress the decomposition of IκB-α, thereby inhibiting signaling related to an inflammatory response caused by p65 (FIG. 3D).

Accordingly, it can be seen that *Bifidobacterium animalis* subsp. *lactis* LM1017 of the present disclosure can inhibit the expression of pro-inflammatory cytokines by regulating the NF-κB signaling pathway, and, thus, the strain of the present disclosure can inhibit an inflammatory response.

Example 5: Evaluation of Ability of *Bifidobacterium animalis* Subsp. *lactis* LM1017 to Decrease Skin Thickness in Atopic Dermatitis Model (In Vivo)

In order to confirm whether *Bifidobacterium animalis* subsp. *lactis* LM1017 as obtained in Example 1 can actually treat dermatitis, such as atopic dermatitis, in an animal, a skin tissue thickness change test, which has been usually used for checking the effect in treating dermatitis in a dermatitis animal model was carried out as follows.

First, laboratory mice were prepared and then exposed to 2,4-dinitrochlorobenzene (DNCB), which is a material that greatly increases the levels of IgE or Th2 cytokines and causes chronic contact dermatitis, to prepare atopic dermatitis models. Each of the mouse models were treated with *Bifidobacterium animalis* subsp. *lactis* LM1017 as obtained in Example 1 at a concentration of $1\times10^9$ cells/g to prepare Example 5. In addition to Example 5, a negative control group (treated with DNCB but not treated with LM1020) and a positive control group (treated with DNCB and dexamethasone (Dex, atopic dermatitis drug)) were prepared with mouse models as Comparative Examples. The skin of the mouse from each of Example and Comparative Examples was collected and subjected to slide staining with H&E to check the skin thickness and thus check the effect in treating dermatitis.

Figure 5A:
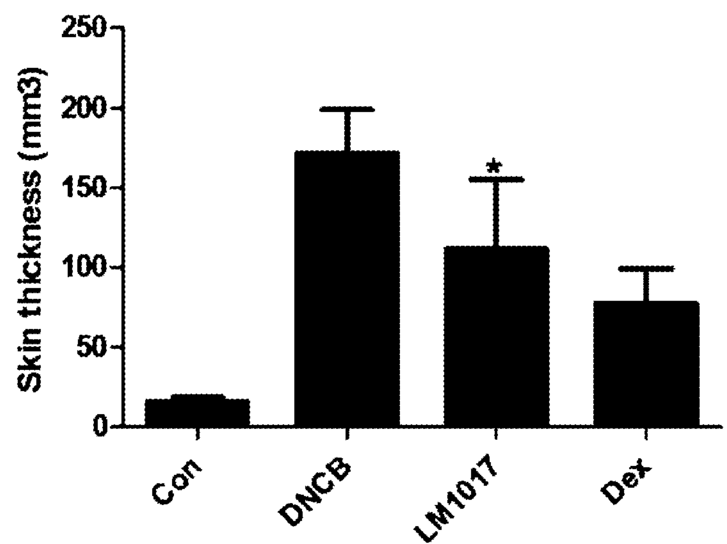
FIG. 5A and FIG. 5B are graphs showing changes in the thickness of the mouse skin treated with *Bifidobacterium animalis* subsp. *lactis* LM1017 according to an example of the present disclosure.
Figure 5B:
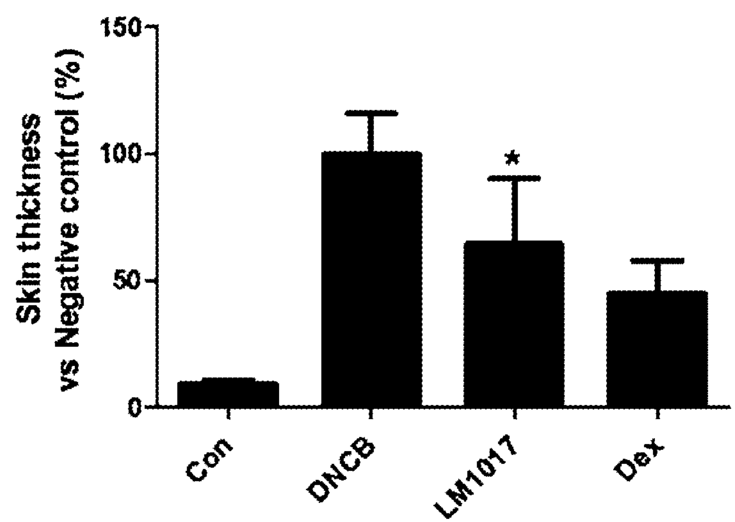
Figure 6A:
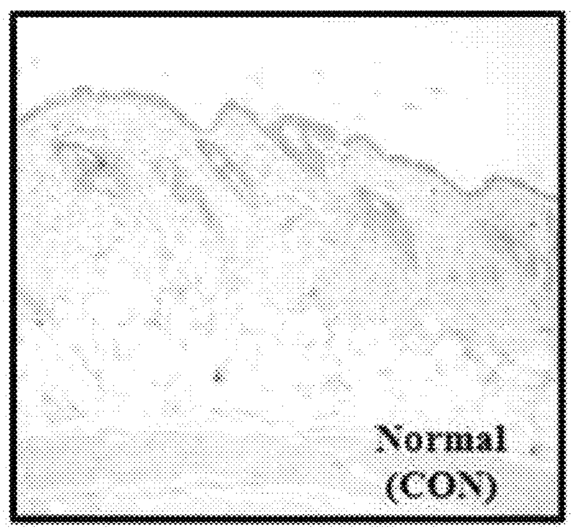
FIG. 6 provides optical microscopy images showing the result of Toluidine blue O staining of the mouse skin treated with *Bifidobacterium animalis* subsp. *lactis* LM1017 according to an example of the present disclosure.
Figure 6B:
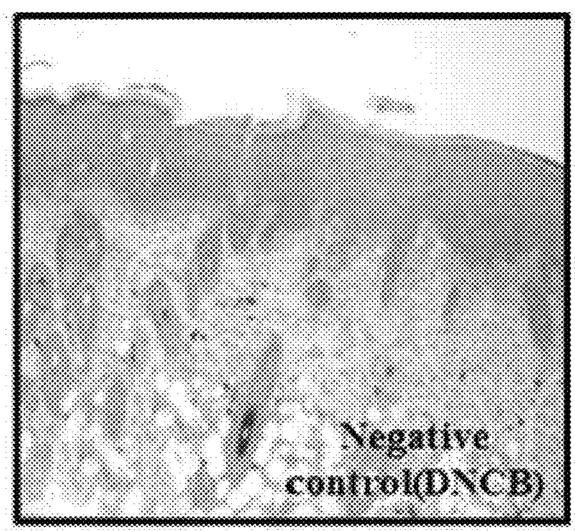
Figure 6C:
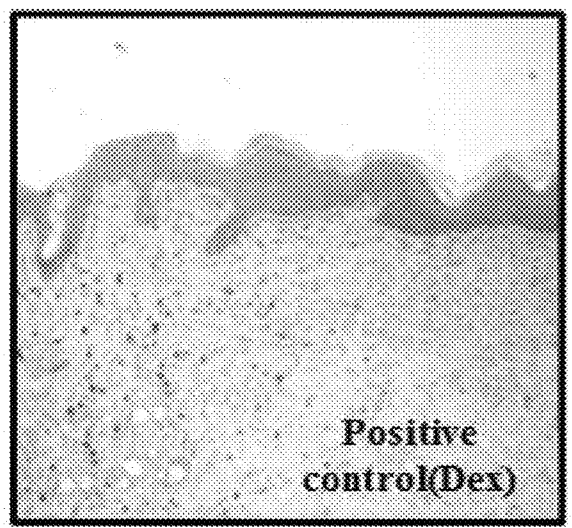
Figure 6D:
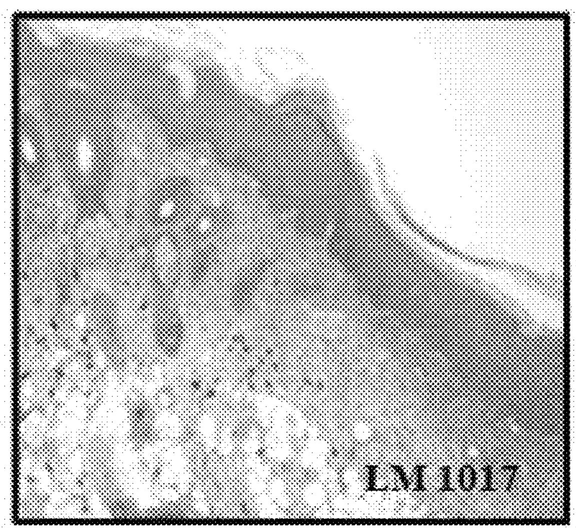

FIG. 4 provides optical microscopy images showing the result of H&E staining of Example and Comparative Examples, and FIG. 5 provides graphs showing a change in the thickness of the mouse skin after staining. According to the test result, it can be seen that the mouse treated with *Bifidobacterium animalis* subsp. *lactis* LM1017 of the present disclosure has a smaller thickness of the hypodermis layer than the mouse from the negative control group, and, thus, LM1017 of the present disclosure is actually effective in treating atopic dermatitis in an animal.

Example 6: Evaluation of Ability of *Bifidobacterium animalis* Subsp. *lactis* LM1017 to Regulate Mast Cells in Atopic Dermatitis Model (In Vivo)

Figure 7A:
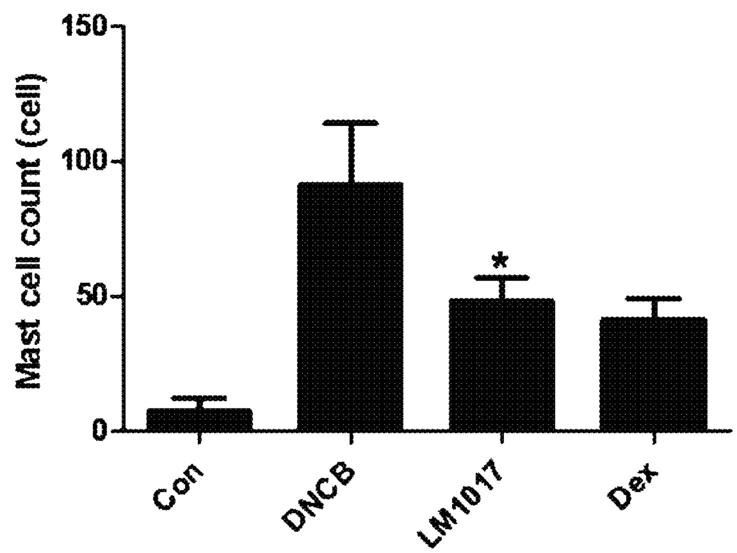
FIG. 7A and FIG. 7B are graphs showing changes in the number of mast cells in the mouse treated with *Bifidobac-*
Figure 7B:
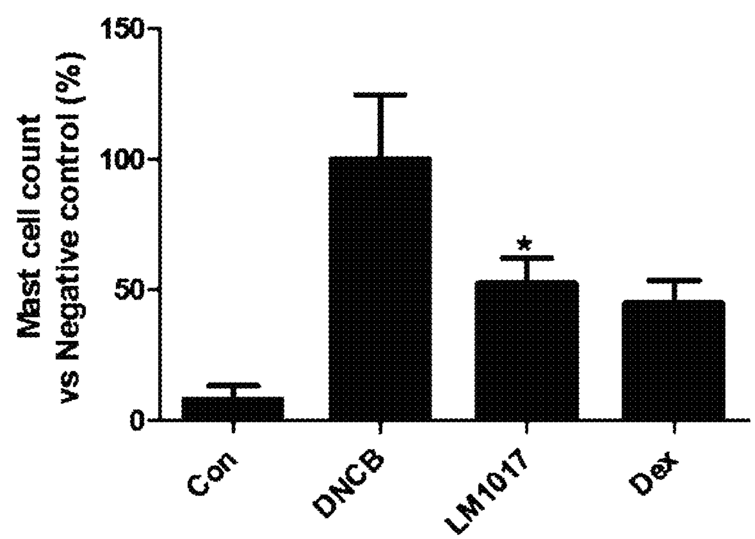

Whether *Bifidobacterium animalis* subsp. *lactis* LM1017 as obtained in Example 1 can actually reduce the number of mast cells related to an inflammatory response in an animal was checked. Specifically, as for *Bifidobacterium animalis* subsp. *lactis* LM1017 (at a concentration of $1\times10^9$ cells/g) and a negative control group (treated with DNCB) and a positive control group (treated with DNCB and dexamethasone (Dex, atopic dermatitis drug)) as Comparative Examples, the mast cells were stained with Toluidine blue O (FIG. 6) and the number of the mast cells was counted using a Toluidine blue marker and shown in the graphs (FIG. 7).

According to the test result, it can be seen that the number of the mast cells of the mouse treated with *Bifidobacterium animalis* subsp. *lactis* LM1017 of the present disclosure is lower than that of the mouse from the negative control group (FIG. 6 and FIG. 7), and, thus, LM1017 of the present disclosure can actually reduce the number of mast cells in an animal and thus can inhibit an inflammatory response, thereby treating atopic dermatitis.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

ACCESSION NUMBER

Depository Institution: Korean Culture Center of Microorganisms (Overseas)

Accession Number: KCCM12629P

Date of Deposit: Nov. 14, 2019

We claim:

1. A composition for the treatment of atopic dermatitis, containing *Bifidobacterium animalis* subsp. *lactis* LM1017 deposited to Korean Culture Center of Microorganisms under the accession number KCCM12629P, wherein the *Bifidobacterium animalis* subsp. *lactis* LM1017 comprises heat-killed bacteria.

2. The composition for the treatment of atopic dermatitis of claim 1, wherein the composition for the treatment of atopic dermatitis contains *Bifidobacterium animalis* subsp. *lactis* LM1017 at a concentration of $1\times10^8$ cells/g to $1\times10^{10}$ cells/g.

3. The composition for the treatment of atopic dermatitis of claim 1, wherein *Bifidobacterium animalis* subsp. *lactis* LM1017 inhibits the expression of inflammatory cytokines by reducing a number of mast cells.

4. The composition for the treatment of atopic dermatitis of claim 1, wherein *Bifidobacterium animalis* subsp. *lactis* LM1017 inhibit an inflammatory response by regulating an NF-κB signaling pathway.

5. A health functional food for the improvement of atopic dermatitis, containing the composition of claim 1 that includes the *Bifidobacterium animalis* subsp. *lactis* LM1017.

6. The composition for the treatment of atopic dermatitis of claim 1, wherein the *Bifidobacterium animalis* subsp. *lactis* LM1017 is the only bacterium in the composition.

* * * * *